United States Patent [19]

Hollander

[11] Patent Number: 4,682,007
[45] Date of Patent: Jul. 21, 1987

[54] DEFOGGING AND DEICING SHIELD STRUCTURE

[76] Inventor: James M. Hollander, Main St., Goshen, Mass. 01032

[21] Appl. No.: 853,169

[22] Filed: Apr. 17, 1986

[51] Int. Cl.$^4$ .............................................. H05B 3/26
[52] U.S. Cl. ...................................... 219/211; 2/435; 219/201; 219/548; 219/203
[58] Field of Search ............... 219/200, 201, 202, 203, 219/211, 213, 528, 548, 549; 350/253, 588; 2/435, 434, 424

[56] References Cited

U.S. PATENT DOCUMENTS

| | | | |
|---|---|---|---|
| 3,024,341 | 3/1962 | Ogle | 219/211 |
| 3,027,561 | 4/1962 | Senne | 2/435 |
| 3,609,293 | 9/1971 | Stewart | 219/200 |
| 4,035,608 | 7/1977 | Stromquist | 219/218 |
| 4,584,721 | 4/1986 | Yamamoto | 2/435 |

FOREIGN PATENT DOCUMENTS

| | | | |
|---|---|---|---|
| 647637 | 7/1937 | Fed. Rep. of Germany | 2/435 |
| 636251 | 5/1983 | Switzerland | 2/435 |
| 264280 | 1/1927 | United Kingdom | 2/435 |
| 2091527 | 7/1982 | United Kingdom | 219/203 |

*Primary Examiner*—E. A. Goldberg
*Assistant Examiner*—Teresa J. Walberg
*Attorney, Agent, or Firm*—Bachman & LaPointe

[57] ABSTRACT

An improved defogging and deicing shield structure suitable for use as a face shield in combination with a protective helmet or for use in goggles having at least two spaced coextensive lenses. The inner surface of one lens is imprinted with an electrical circuit in a predetermined pattern. The resistance of the circuit being sufficient to generate heat effective to defog or deice the exterior surface of the other lens when the circuit is connected to a direct current power source.

19 Claims, 5 Drawing Figures

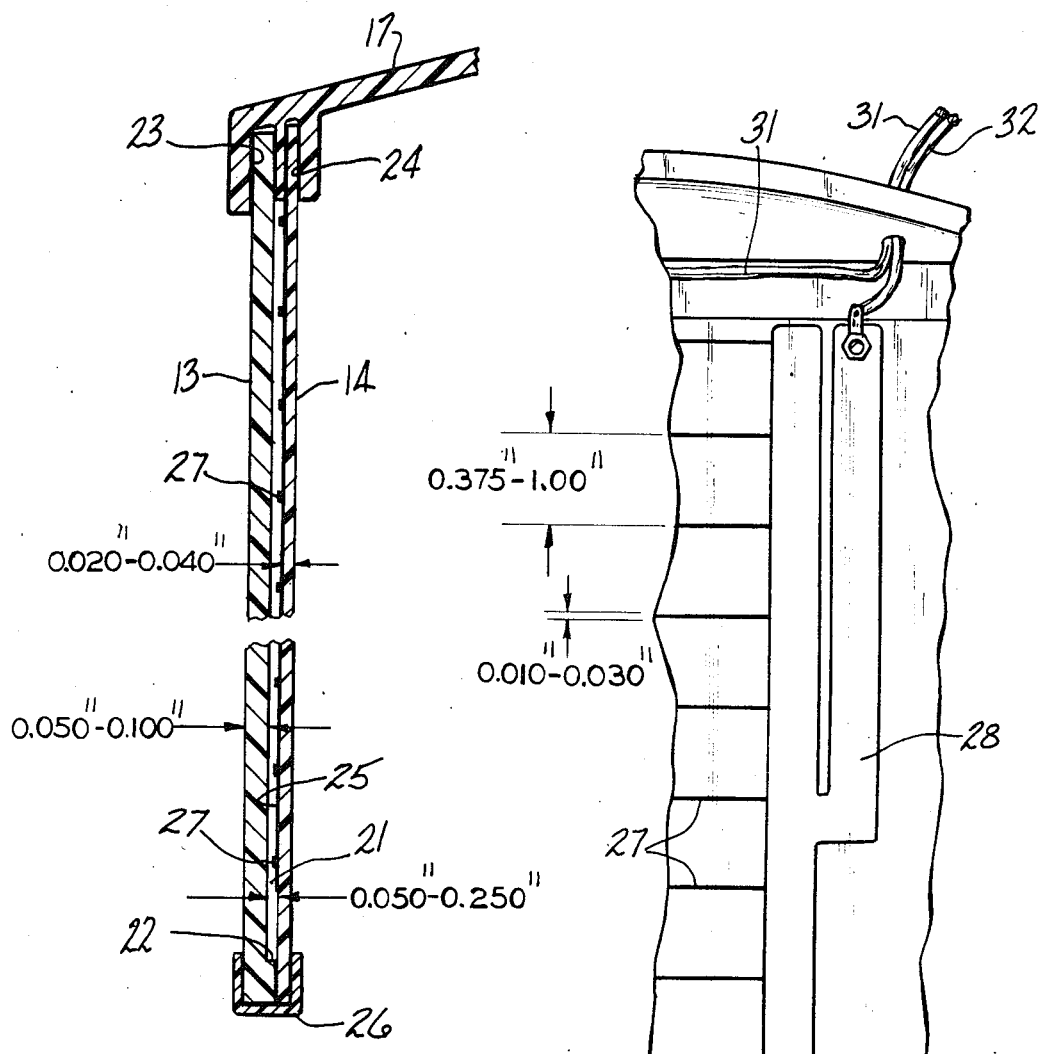
FIG-3
FIG-4
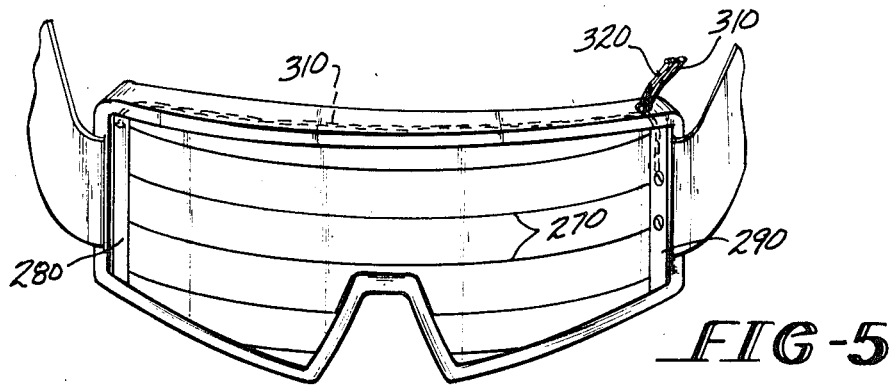
FIG-5

DEFOGGING AND DEICING SHIELD STRUCTURE

CROSS-REFERENCE TO RELATED APPLICATION

This application is related to a copending design application Ser. No. 842,006 filed Mar. 6, 1986 bearing Attorney's docket No. 86-134 by James Hollander entitled Face Shield.

BACKGROUND OF THE INVENTION

The present invention relates to shield structures and relates, in particular, to such structures which are useful in combination with a protective helmet or in goggles including means incorporated in the shield for effecting a defogging or a deicing function.

PRIOR ART

Prior art shield structures are disclosed and described in U.S. Pat. Nos. 3,024,341 issued Mar. 6, 1962 to Ogle et al. entitled Heated Face Plate For Pilot's Helmet, 3,727,235 issued Apr. 17, 1973 to Fisher entitled Retractable Face Protective Assembly and 4,575,875 issued Mar. 18, 1986 to Dawson et al. entitled Detachable Visor For A Motorcycle Helmet.

The '341 patent discloses an electrically conductive transparent film deposited on a transparent visor of an aircraft helmet. Alternatively, the film is sandwiched between two transparent laminated sheets.

The '235 patent shows a single lens shield which is releasably attached to a helmet and includes means for effecting relative motion between the shield and the helmet. As is most apparent in FIGS. 19 and 20 the shield includes a defogging means 426 comprising air flow directing panel means 450.

The '875 patent shows a detachable visor 10 having a recess 32 facilitating attachment of the visor to the helmet. The recess is then filled with a panel 40. An air flow deflector panel 50 is attached to the underside of the visor.

While electrically conductive films are operative to defog aircraft helmets the films usually create a tinting effect reducing light transmission with some reduction in visibility. Without doubt, these losses present no problem and, in fact, are probably an aid to a flyer ranging high above clouds where one needs protection from the bright sun.

In contrast, shield requirements in surface applications including night operations require maximum light transmission with maximum visibility.

SUMMARY OF THE INVENTION

Consequently, it is a principal object of the present invention to provide a shield structure useful in combination with a helmet or in goggles which inhibits the formation of fog, ice or frost upon the shield while providing maximum light transmission and maxiumum visibility, day and night.

A further feature of the invention is the provision of a shield structure comprising at least two lenses spaced apart by an air gap.

A further feature of the invention is the provision of a multi-lens shield structure or device in which the inner face of one lens is inprinted with an electrically conductive circuit arranged in a predetermined pattern to provide maximum light transmission and good visibility to the user.

A still further feature of the invention is the provision of a shield device having a relatively heavy gauge weather lens spaced from a relatively light gauge face lens.

A further feature of the invention is the provision of a printed electrically conductive circuit on the inner surface of the face lens.

A still further feature of the invention is the provision of a thermal insulating barrier in the form of a gap between the face lens and the weather lens to minimize heat loss through the weather lens.

A shield structure for defogging, deicing, and defrosting embracing certain features of the present invention may comprise at least two spaced lenses one lens defining a face lens and another lens defining a weather lens one of said lenses being imprinted, with an electrically conductive circuit, said circuit being arranged upon said lens in accordance with a predetermined pattern.

The term "lens" is intended to denote sheets or plates of relatively flexible, highly transparent material having planar or curved surfaces usually fabricated from synthetic compounds.

Other features and advantages of the present invention will become more apparent from an examination of the succeeding specification when read in conjunction with the appended drawings, in which:

BRIEF DESCRIPTION OF THE DRAWINGS

FIG. 3 is a vertical section of the shield device of FIG. 2 taken along the line 3—3 and as viewed in the direction of the arrows.

FIG. 4 is a partial view, enlarged, of the interior of the left side of FIG. 2, and, FIG. 5 shows a goggle embodiment of the shield structure.

DESCRIPTION OF THE PREFERRED EMBODIMENT

Figure 1:
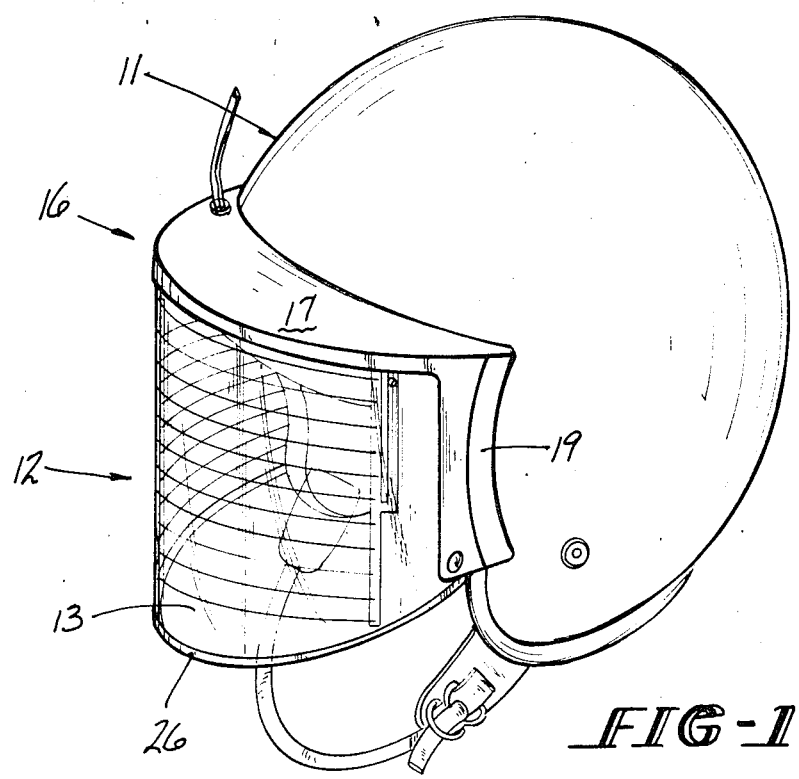
FIG. 1 is a perspective view of the shield device of the present invention assembled to a helmet.

Referring to the drawings in particular in FIGS. 1, 2, 3 and 4 reference numeral 11 designates a helmet having a face shield 12. The shield 12 is releasably attached to the helmet and is movable relative to the helmet in well known fashion.

The shield includes a weather lens 13 and a face lens 14 supported in a visor 16 having a peak 17 and sidewalls 18 and 19.

The weather lens has a thickness ranging from 0.050 to 0.100 inches and the face lens has a thickness ranging from 0.020 to 0.040 inches.

Preferably the lenses are fabricated from synthetic materials such as polycarbonate, butyrate or acrylic resins.

The lenses 13 and 14 are spaced apart to define an air gap 21 providing a thermal insulator between lenses.

Spacing between lenses is maintained by peripheral spacer means which is developed in several ways.

For example, one portion of the periphery of the shield includes a bead or spacer 22 molded integrally with the weather lens.

Spacing is maintained at the top of the shield by slots formed in the underside of the peak. That is, weather lens 13 engages slot 23 and face lens 14 engages slot 24.

To enhance durability and increase strength the respective lenses may also be fitted into slots formed in the visor sidewalls 18 and 19.

It is also within contemplation of the invention to use spacer means in the form of a separate gasket-like member of a thickness sufficient to maintain desired spacing between lenses.

It is desirable to maintain an air gap between lenses ranging from 0.050 to 0.250 inches.

Figure 2:
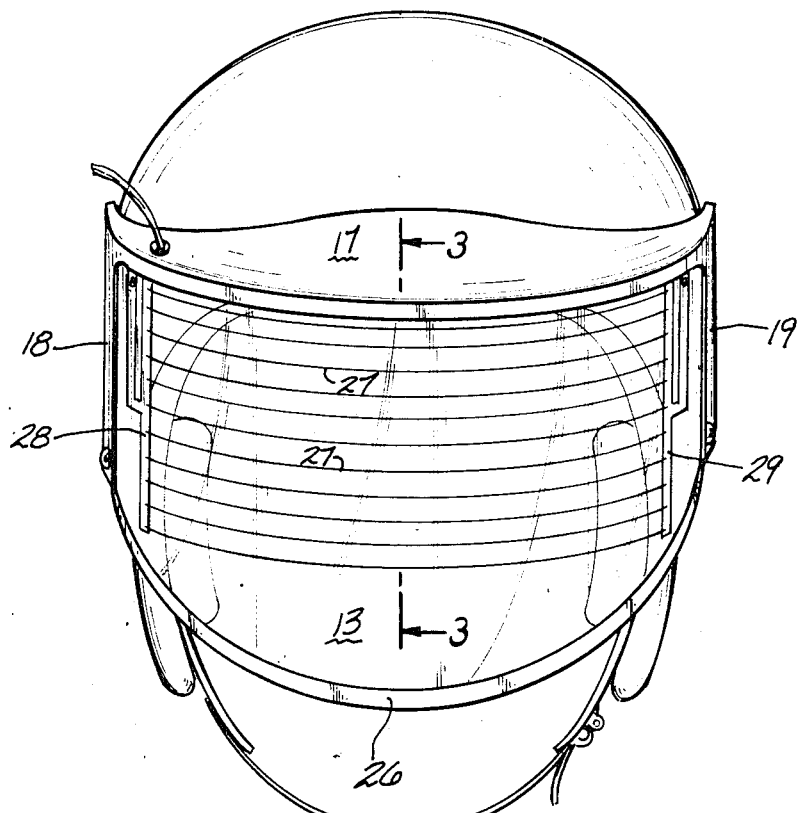
FIG. 2 is a front elevational view of the illustration of FIG. 1.

In order to seal the air space or air gap 21 against undesirable particulate and liquid matter from the atmosphere a seal means such as an adhesive or other suitable bonding agent is applied between the peripheral bead (or gasket-like material, as the case may be) and the lenses. Alternatively, the seal means may take the form of adhesive tape 26 as shown in FIGS. 2 and 3.

An electrically conductive circuit is imprinted by silk screening or similar procedures upon the inner surface 25 of the face lens 14 defining a predetermined pattern of circuitry. The pattern takes the form of generally parallel lines 27—27 spanning the shield and joining bus bars 28 and 29 at the extremities of the lines.

Each line has a width ranging from 0.010 to 0.030 inches, a thickness of less than 0.0005 inches and are spaced vertically at a distance ranging from 0.375 to 1.00 inches measured from center to center of each line. Thus, at maximum width (0.030 inches) and at minimum spacing (0.375 inches) lines of conductivity occupy no more than about 8%, per unit area, of the field of view of the face shield.

The circuit is printed with an ink having a metalic content calculated to create an optimum resistance and an optimum power density per unit area.

For example, a 7.2 ohm resistance circuit will produce 20 watts over a 50 square inch area creating an optimum power density of 0.40 watts per square inch of shield area when energized by a typical twelve (12) volt a.c. or d.c. current power source. A power density ranging from 0.30 to 0.60 watts per square inch is operable.

This circuitry generates heat in the air space or air gap 21 keeping the face lens free of fog created by heavy breathing while defogging, deicing and defrosting the weather lens. The weather lens in combination with the insulating air gap minimizes heat loss to atmosphere.

The electrical circuit is completed by imprinted bus bars 28 and 29 connected to insulated conductors 31 and 32, respectively. The conductors 31 and 32 are connected to a power source such as a 12 volt a.c. or d.c. power source (not shown).

If suitable, the length of conductor 31 can be reduced by extending the bus bar 28 across the upper end of the face shield.

If desirable, a switch means may be included in the circuitry calling for "on" or "off" as well as "high" and "low" power.

The FIG. 5 embodiment of the invention discloses the shield device in a goggle application where the circuitry includes imprinted conductors 270—270, bus bars 280 and 290 insulated conductors 310 and 320 connected to a suitable a.c. or d.c. power source.

The lens structure of the goggles of FIG. 5 is generally the same as that of the shield 12 on a smaller scale.

It is to be understood that the invention is not limited to the illustrations described and shown herein, which are deemed to be merely illustrative of the best modes of carrying out the invention, and which are susceptble of modification of form, size, arrangement of parts and details of operation. The invention rather is intended to encompass all such modifications which are within its spirit and scope as defined by the claims.

What is claimed is:

1. In a protective helmet and face shield assembly including fastener means for securing the shield releasably to the helmet and hinge means between the fastener means and the shield permitting relative motion between the shield and the helmet an improved face shield comprising:

at least two spaced, plastic lenses providing a field of view, one lens defining a face lens and another lens defining a weather lens, a surface of one of said lenses being imprinted solely by silk screening with an electrically conductive circuit substantially throughout said field of view, said circuit being arranged upon said surface in accordance with a pattern of spaced, continuous, generally parallel lines, said lines at maximum width and minimum spacing occupying no more than about eight percent (8%), per unit area, of said field of view, said field of view being otherwise free of coatings or films.

2. The assembly of claim 1 in which the lenses are coextensive and the region between the spaced lenses defines an air space.

3. The assembly of claim 2 in which the air space defines a thermal insulator blocking excessive heat loss through the weather lens and minimizing power consumption.

4. The assembly of claim 2 in which the periphery of the coextensive lenses is provided with seal means protecting the air space against undersirable exterior fluid and particulate matter.

5. The assembly of claim 4 in which the seal means includes an elongated peripheral spacer formed integrally with one of said lenses.

6. The assembly of claim 5 in which the seal means comprises a combination of said spacer and a suitable adhesive or bonding agent.

7. The assembly of claim 1 in which the circuit is imprinted upon an inner surface of one of said lenses.

8. The assembly of claim 7 in which the circuit is imprinted upon the inner surface of the face lens.

9. The assembly of claim 8 in which the imprinted electrical circuit develops sufficient resistance to electrical current to create heat in said air space.

10. the assembly of claim 9 in which the imprinted circuit develops a power density throughout said one of said lenses when energized by a 12 volt a.c. or d.c. power source effective to create heat sufficient to eliminate fog or mist and to melt snow, ice, slush and the like accumulating on the outer surface of the weather lens.

11. The assembly of claim 10 in which the material from which the lenses are fabricated and the power density are selected to optimize defogging and deicing without deleterious effect upon the lens material.

12. The assembly of claim 10 in which the power density ranges from 0.30 to 0.60 watts per square inch of face lens within said circuit pattern.

13. The assembly of claim 12 in which the material from which the face lens is manufactured is selected from the group consisting of polycarbonates, butyrate and acrylics.

14. The assembly of claim 1 in which the imprinted circuit includes opposed bus bars each connected to an insulated electrical conductor and the conductors lead to an a.c. or a d.c. power source.

15. The assembly of claim 14 in which one insulated conductor is replaced partially by an extension of one bus bar.

16. The assembly of claim 1 in which a portion of the pattern includes spaced parallel lines having a width ranging from 0.010 to 0.030 inches, a thickness less than 0.0005 inches and are spaced apart a distance ranging from 0.375 to 1.00 inches measured from the center of each line.

17. The face shield of claim 1 in which the weather lens is of a thickness ranging from 0.050 to 0.100 inches and the face lens is of a thickness ranging from 0.020 to 0.040 inches.

18. A face shield comprising at least two plastic lenses, one lens defining a face lens and another lens defining a weather lens, said lenses being coextensive and being separated by spacer means defining an appreciable air gap between lenses, the inner surface of one lens being imprinted with an electrically conductive circuit arranged in accordance with a predetermined pattern, said pattern defining spaced parallel lines or ribbons of printed indicia where the lines range in width from 0.010 to 0.030 inches and in thickness less than 0.0005 inches and are spaced apart, a distance ranging from 0.375 to 1.00 inches measured from the center of each line or ribbon, said circuit having sufficient electrical resistance to create heat effective to warm the other lens when connected to a 12 volt a.c. or d.c. power source.

19. A defogging and deicing shield structure in the form of goggles comprising at least two plastic lenses, defining an eye lens and a weather lens, spacer means for creating an air gap between lenses, an electrically conductive circuit imprinted on an inner surface of said eye lens effective to warm said air space and said weather lens when said circuit is connected to a 12 volt source of a.c. or d.c. current, said circuit defining spaced parallel lines or ribbons of printed indicia where the lines range in width from 0.010 to 0.030 inches and in thickness less than 0.0005 inches and are spaced apart, a distance ranging from 0.375 to 1.00 inches measured from the center of each line or ribbon.

* * * * *